United States Patent
Stanley et al.

(10) Patent No.: US 8,818,637 B2
(45) Date of Patent: Aug. 26, 2014

(54) OCCUPANT CLASSIFICATION SYSTEM

(75) Inventors: James G. Stanley, Novi, MI (US); George Theos, West Bloomfield, MI (US); Phil Maguire, Royal Oak, MI (US); Don McDonald, Howell, MI (US)

(73) Assignee: TK Holdings Inc., Auburn Hills, MI (US)

( * ) Notice: Subject to any disclaimer, the term of this patent is extended or adjusted under 35 U.S.C. 154(b) by 584 days.

(21) Appl. No.: 11/698,303

(22) Filed: Jan. 26, 2007

(65) Prior Publication Data

US 2007/0192007 A1 Aug. 16, 2007

Related U.S. Application Data

(60) Provisional application No. 60/762,124, filed on Jan. 26, 2006, provisional application No. 60/824,001, filed on Aug. 30, 2006.

(51) Int. Cl.
*B60R 21/015* (2006.01)
*B60R 22/00* (2006.01)
*B60N 2/44* (2006.01)

(52) U.S. Cl.
USPC .......................................................... 701/45

(58) Field of Classification Search
USPC .................. 701/29, 36, 45–47; 180/271–273; 280/728.1, 734, 735; 340/536, 340/561–563, 663
See application file for complete search history.

(56) References Cited

U.S. PATENT DOCUMENTS

| | | | |
|---|---|---|---|
| 4,814,696 A | | 3/1989 | Kern et al. |
| 6,043,743 A * | | 3/2000 | Saito et al. .................... 340/562 |
| 6,392,542 B1 * | | 5/2002 | Stanley ........................ 340/561 |
| 6,442,504 B1 * | | 8/2002 | Breed et al. .................... 702/173 |
| 6,609,054 B2 * | | 8/2003 | Wallace .......................... 701/45 |
| 6,696,948 B2 * | | 2/2004 | Thompson et al. .......... 340/561 |
| 6,816,077 B1 * | | 11/2004 | Shieh et al. .................... 340/602 |
| 6,825,765 B2 * | | 11/2004 | Stanley et al. ................ 340/561 |
| 7,026,946 B2 * | | 4/2006 | Saunders et al. ............. 340/666 |
| 7,046,158 B2 * | | 5/2006 | Saunders et al. ............. 340/666 |
| 7,082,360 B2 * | | 7/2006 | Oestreicher et al. ........... 701/45 |
| 7,084,763 B2 * | | 8/2006 | Shieh et al. .................... 340/561 |
| 7,102,527 B2 * | | 9/2006 | Shieh et al. .................... 340/602 |
| 7,225,067 B2 * | | 5/2007 | Sleboda et al. ................. 701/36 |
| 7,271,730 B2 * | | 9/2007 | Kimura et al. ................ 340/667 |
| 7,436,299 B2 * | | 10/2008 | Shieh et al. .................... 340/561 |
| 7,548,808 B2 * | | 6/2009 | Winkler .......................... 701/45 |

(Continued)

FOREIGN PATENT DOCUMENTS

DE 41 10 702 A1 10/1992
WO WO 01/92900 12/2001

*Primary Examiner* — Helal A Algahaim
*Assistant Examiner* — Charles J Han
(74) *Attorney, Agent, or Firm* — Foley & Lardner LLP

(57) ABSTRACT

An occupant classification system classifies occupants on a vehicle seat and is capable of separating child seats from adults during wet seat cases. In the system, the seat structure is grounded. The classification system includes a measurement circuit, an identifying circuit, and a controller. The measurement circuit is configured to measure in-phase and quadrature components of a current sent out to the sensing element. The identifying circuit is configured to identify if a seat pan and a seat back frame of the vehicle seat are grounded to a circuit ground. The controller is configured to use measurements of the measurement circuit to classify the occupant. The sensing element can be located in a sensing mat that further includes a heating element.

22 Claims, 6 Drawing Sheets

(56) References Cited

U.S. PATENT DOCUMENTS

| | | |
|---|---|---|
| 7,656,169 B2 * | 2/2010 | Scheckenbach et al. ..... 324/679 |
| 2002/0120379 A1 * | 8/2002 | Oestreicher et al. ............ 701/45 |
| 2003/0090376 A1 * | 5/2003 | Thompson et al. ........... 340/541 |
| 2003/0122669 A1 * | 7/2003 | Filippov et al. ............... 340/563 |
| 2004/0111201 A1 * | 6/2004 | Thompson et al. ............. 701/45 |
| 2004/0196150 A1 * | 10/2004 | Shieh et al. ................... 340/501 |
| 2004/0199318 A1 * | 10/2004 | Shieh et al. ..................... 701/45 |
| 2005/0253712 A1 * | 11/2005 | Kimura et al. ................ 340/562 |
| 2005/0275202 A1 * | 12/2005 | Wato et al. .................... 280/735 |
| 2006/0164254 A1 * | 7/2006 | Kamizono et al. ............ 340/667 |
| 2006/0187038 A1 * | 8/2006 | Shieh et al. ................... 340/562 |
| 2007/0182553 A1 * | 8/2007 | Kamizono et al. ............ 340/561 |

\* cited by examiner

OCCUPANT CLASSIFICATION SYSTEM

CROSS-REFERENCE TO RELATED PATENT APPLICATIONS

This application claims priority to U.S. Provisional Patent Application Nos. 60/762,124 filed Jan. 26, 2006, and 60/824,001 filed Aug. 30, 2006, both of which are incorporated herein by reference in its entirety

BACKGROUND

The present invention relates to occupant classification systems (OCS) for vehicles. Occupant classification systems are used in vehicles to determine what type of occupant (e.g., adult, child, or infant) is present in the vehicle.

When a vehicle seat is wet, a loading current out of the sensing electrode increases. When a rear facing infant seat (RFIS) contains an infant during a wet seat situation (RFIS/wet), the current out to the electrode may be higher than an adult occupant situation. With a system that only measures the current amplitude out to the sensing electrode, there may be a problematic overlap between the child seat cases and the adult cases.

Some conventional systems, a seat pan and seat back frame may be grounded because of a connection through seat tracks and a seat back angle adjuster to the floor pan. However, these grounding systems can be unreliable.

In vehicles with heated seats, occupant classification systems that are packaged in the vehicle seat above the seat foam must work in close proximity to a seat heater. When occupant classification systems use capacitive sensing or electric field sensing, a seat heater can have a significant affect on the measurements of the OCS. Some conventional systems require that the heater "float" when capacitive sensing measurements are being obtained. In this context, floating means that the heater element has a high impedance to ground. Because the impedance being measured is capacitive in nature, even a small capacitive coupling (>several pF) between the heating element and ground can have an important impact on the capacitive sensing measurements.

In general, it is difficult to "float" the heater consistently. If the heater element is not floating, the mechanical orientation between the sensing element and the heating element can significantly affect the overall response of the system. For example, over the life of a vehicle, the orientation between the heater and capacitive sensor may change. The change in orientation between a heater element and the capacitive sensing element will also affect the performance of an occupant classification system.

In other conventional systems, separate mats for the heater and sensor element are used. Disadvantages to this configuration include the inconvenience of an additional installation process, having additional insulation between the heater and the seat surface, having an extra layer (possibly a shielding layer) between the sensor and the seat surface and having numerous other sources of system interaction.

In another known occupant classification system, the seat heater element also functions as the sensor element. In this system the sensing and heating operations are time multiplexed. The sensor takes about 10% of the available time to make measurements and the remaining 90% of the operational time is used to heat the seat. A drawback to this system is that the sensing electrode is significantly influenced by the heating control electronics. In addition, there is no physical barrier or separation between the heating and sensing ECU.

SUMMARY

One exemplary embodiment relates to an occupant classification system. The classification system comprises: a sensing element in a vehicle seat, the sensing element comprises a sensing electrode; a measurement circuit that is configured to measure in-phase and quadrature components of a current sent out to the sensing electrode; a circuit that is configured to identify if a seat pan or seat back frame of the vehicle seat are grounded to a circuit ground; and a controller that is configured to classify an occupant by using measurements of the measurement circuit.

Another exemplary embodiment relates to an occupant classification system. The classification system comprises: a sensing element in a vehicle seat, the sensing element comprises a sensing electrode; a measurement circuit that is configured to measure a current sent out to the sensing electrode; at least one wire that connects a seat pan or seat back frame of the vehicle seat to a circuit ground or a chassis ground; and a controller that is configured to classify the occupant by using measurements of the measurement circuit.

A further exemplary embodiment relates to an occupant classification system. The system comprises: a vehicle seat with a seat pan and a seat back frame; a sensing element in a vehicle seat, the sensing element comprises a sensing electrode; a measurement circuit to measure current sent to the sensing electrode; a circuit to identify if the seat pan or seat back frame are grounded to a circuit ground; and a controller to classify an occupant of the vehicle seat using measurements from the measurement circuit. During a wet seat situation, the controller is configured to separate an adult from a child seat when classifying the occupant.

A further exemplary embodiment relates to an occupant classification system. The system comprises: a sensing element in a vehicle seat; a measurement circuit that is configured to measure in-phase and quadrature components of a current sent out to the sensing element; a circuit that is configured to identify if a seat pan or seat back frame of the vehicle seat are grounded to a circuit ground; and a controller that is configured to classify an occupant by using measurements of the measurement circuit. During a wet seat situation, the controller is configured to separate a classification of an adult from a child seat when classifying the occupant of the vehicle seat.

A further exemplary embodiment relates to an occupant classification system. The system comprises: a sensing mat; a sensing element formed in the sensing mat; and a heating element formed in the sensing mat. The sensing element and heating element are positioned a predetermined distance apart.

A further exemplary embodiment relates to an occupant classification system for a vehicle. The system comprises: a sensing mat with a conducting sensing electrode; a controller that is configured to perform electric field measurements near the sensing mat; and at least one wire to connect the controller to at least one additional conductor. Potential of the at least one additional conductor influences the electric field near the sensing mat. The controller includes a mechanism to provide a low impedance between the at least one additional conductor and a controller circuit ground.

It is to be understood that both the foregoing general description and the following detailed description are exemplary and explanatory only, and are not restrictive of the invention as claimed.

BRIEF DESCRIPTION OF THE DRAWINGS

These and other features, aspects, and advantages of the present invention will become apparent from the following description, appended claims, and the accompanying exemplary embodiments shown in the drawings, which are briefly described below.

DETAILED DESCRIPTION

Figure 1:
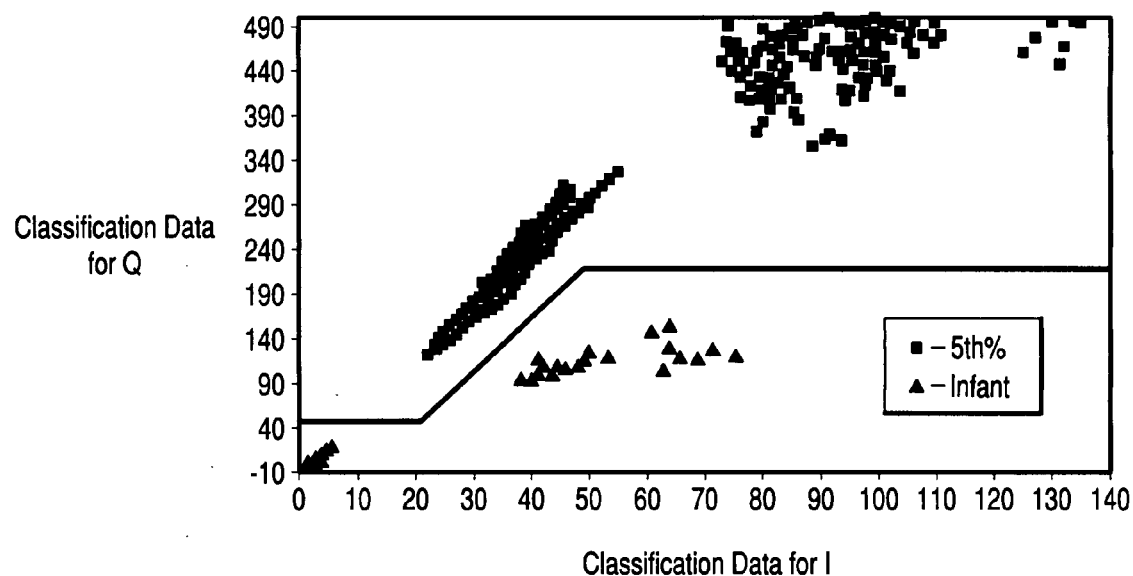
FIG. 1 is a graph showing separation between fifth percent adults and infants during many conditions, including wet seat conditions; the X-axis shows the quadrature component and the Y-axis shows the in-phase component of the measurement.

An embodiment addresses an occupant classification system that includes, among other possible things: a sensing element in a vehicle seat; a measurement circuit that is configured to measure in-phase and quadrature components of a current out to the sensing element; a circuit that is configured to identify if a seat pan and a seat back frame of the vehicle seat are grounded to a circuit ground; and a controller that is configured to use the measurements to classify the occupant.

In a further embodiment of this occupant classification system, the sensing element includes a sensing electrode that is insulated from seat foam and a seat cover of the vehicle seat.

In another further embodiment of this occupant classification system, the sensing electrode may be made from insulated wire.

In another further embodiment of this occupant classification system, the sensing electrode may be a conductor that has been deposited on a carrier.

In another embodiment of this occupant classification system, the sensing element is provided in a sensing mat in the vehicle seat.

In yet another embodiment, the sensing mat further includes a heating element.

Another embodiment addresses an occupant classification system that includes, among other possible things: a sensing mat in a vehicle seat; a sensor element in the sensing mat; and a heating element located in the sensing mat, in which the sensing element and heating element are positioned a predetermined distance apart.

Embodiments will be described with reference to the drawings. Like numbers are used throughout the drawings to refer to the same or similar parts in each of the embodiments of the invention described herein.

A capacitive sensing system sends a time varying voltage out to a single sensing element (sometimes referred to as a "sensor") 270 and measures the loading current to ground 230 from the sensing element 270. In an embodiment, the sensing element 270 comprises a sensing electrode 270. The time varying voltage could take many shapes, although a preferred shape is a sinusoidal signal at frequencies between about 50 kHz and about 150 kHz. This loading current increases significantly when an adult occupant is on the seat and only slightly when there is a child seat on the vehicle seat.

Embodiments utilize a measurement system that measures the in-phase (I) and quadrature (Q) components of the current out to the sensing electrode 270. With such a measurement system, separation remains between the adult and the RFIS/wet situation. Thus, the sensor system can distinguish between an adult and an RFIS on the seat in normal and wet seat situations. Embodiments use the I and Q measurements, seal the sensing electrodes 270 from direct contact with the wet seat foam of the vehicle seat 100, and ensure that the seat structure is grounded to allow separation between the RFIS/wet and normally seated adult cases.

Embodiments of the system can use both the I and Q measurements measured by a current measurement circuit 240, which sends the I and Q measurements to a microprocessor 250, to make a classification of the occupant during wet seat situations because the nature of the impedance to ground changes when the seat 100 is wet. FIG. 1 shows measurement results of a system when the set cover and seat foam of the vehicle seat 100 are wet. Without both I and Q, there would be overlap between the RFIS (infant cases) and small adults (the "standard small adult" are referred to as "5th %" cases, which are occupants approximately 108 lbs.). With I and Q measurements, there is a recognized separation between the RFIS cases and the small adult cases.

In FIG. 1, the measurement results illustrate the I and Q measurements taken over a sample that includes two seat designs in which three cloth seats and two leather seats were utilized. The measurements were taken both during wet seat situations and dry (normal) situations in which the occupants were seated in a normal seating position on the seat 100 (i.e., the occupant is not in an out-of-position situation). The occupants include small adults and RFIS with infants.

In an embodiment, it is not critical that I and Q measurements are made for the system to work. For example, the phase and amplitude of the current sent to the sensing electrode 270 could be measured to gain equivalent information. According to an embodiment, the impedance from the sensing electrode 270 to ground should be characterized such that capacitive components of the impedance affect the measurement differently than the resistive components of the impedance.

According to an embodiment, time varying shapes may be used that are not sinusoidal signals for the sensing. If this is the case, alternative methods of identifying the characteristics of the impedance could be used. For example, square pulses could be sent out to the sensing electrode 270. The current sent out to the sensing electrode 270 could be measured and characteristics such as the peak and rise time of the current pulse could be used to characterize the sensing electrode's 270 impedance to ground 230. Alternatively, several pulses of different length could be sent out to the sensing electrode 270. Characteristics of the impedance could be derived by analyzing the relationship between the peak currents and the variation of the current with pulse length.

The seat 100 should be grounded so that there is a consistent path to ground 230 for the displacement currents flowing from the sensing electrode 270. If the seat pan 110, for example, is grounded when the seat 100 is calibrated (i.e., the empty seat offset is measured) and then the seat pan 110 becomes ungrounded, a small adult could be mistakenly classified as a child seat. The seat back frame 120 is also an important contributor to the seat measurement offset, and whether the seat back frame 120 is grounded is important to the classification results. The seat 100 may also include additional conductive seat parts 130, which may be grounded.

Figure 2:
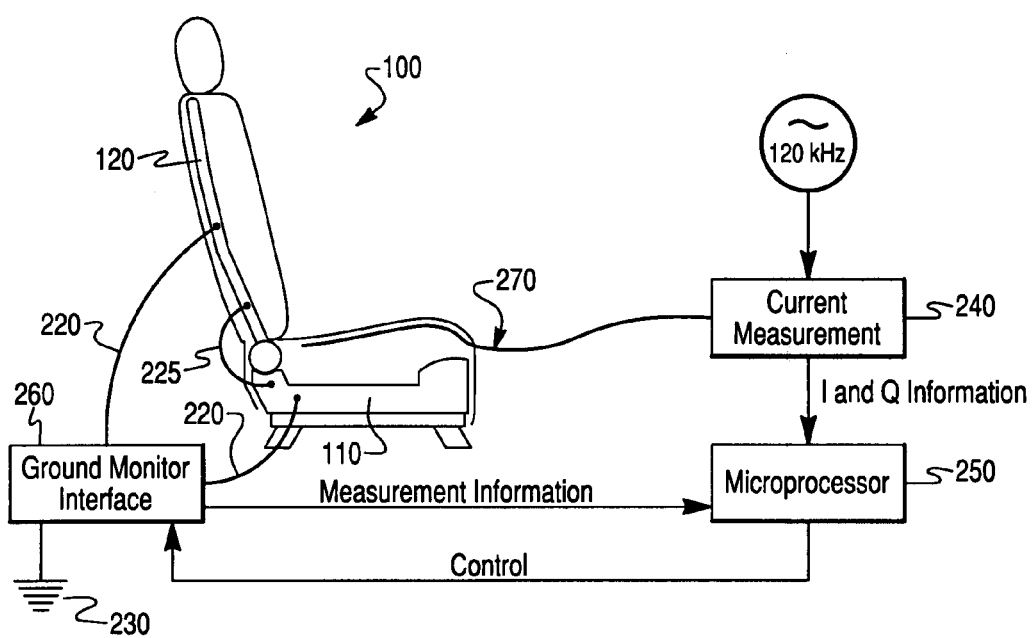
FIG. 2 is a schematic diagram showing blocks used to make measurements and guarantee that a seat is grounded.
Figure 3A:
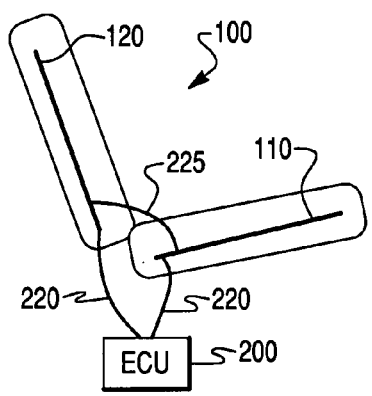
FIG. 3(a) illustrates a grounding scenario for a seat pan and seat back frame according to an embodiment.
Figure 3B:
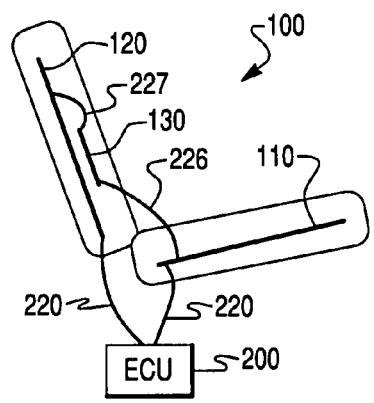
FIG. 3(b) illustrates a grounding scenario for a seat pan and a seat back frame according to another embodiment.
Figure 3C:
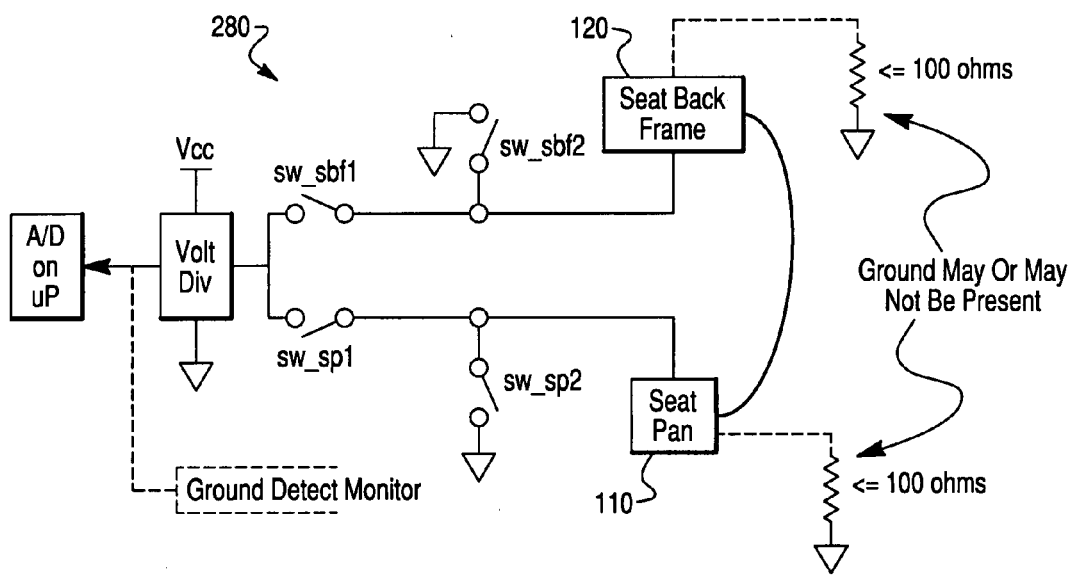
FIG. 3(c) illustrates a ground monitoring circuit according to an embodiment.

Embodiments use a ground monitoring system to verify that the seat pan and the set back frame are both grounded during the measurements, such as the system shown in FIG. 2. The system may include a system electronic control unit (ECU) 200, which is shown in FIG. 3(*a*). The ECU 200 houses the ground monitor interface 260, the microprocessor 250, and current measurement 240 illustrated in FIG. 2. The ECU 200 may also house other components. The ground 230 going into the ground monitor interface 260 may be a circuit ground (or chassis ground) from the vehicle wiring harness (not shown). This configuration shows the wires 220 that go from the ground monitor interface 260 to the seat pan 110 and the seat back frame 120. An additional wire 225 extends from the seat pan 110 to the seat back frame 120. The wires 220 going from the ECU 200 to the seat pan 110 and seat back frame 120 are configured to ensure that the seat pan 110 and seat back frame 120 are grounded during any measurements for occupant classification.

Although a single wire 220 from the ECU 200 to the seat pan 110 can be used to ground the seat pan 110 and/or seat back 120, there is a potential failure mode if the wire 220 is not actually attached to the seat pan 110 and/or seat back 120. If the grounding wires 220 are broken, the ECU's 200 attempt to ground the seat pan 110 and/or seat back 120 would actually only ground the wires 220. The wire 225 going from the seat pan 110 to the seat back 120 can be used, with a ground monitoring circuit 280, to identify cases in which the seat pan 110 and/or seat back frame 120 are not grounded and that at least one of the grounding wires 220 to seat pan 110 and/or seat back frame 120 is not connected (such as shown in FIGS. 2 and 3(*a*)). The ground monitoring circuit 280 is shown in FIG. 3(*c*).

If the seat 100 includes additional conductive parts 130 that could be grounded (such as shown in FIG. 3(*b*), additional wires 226, 227 may be used to put these parts 130 in series with the seat pan 110 and seat back frame 120.

Figure 4:
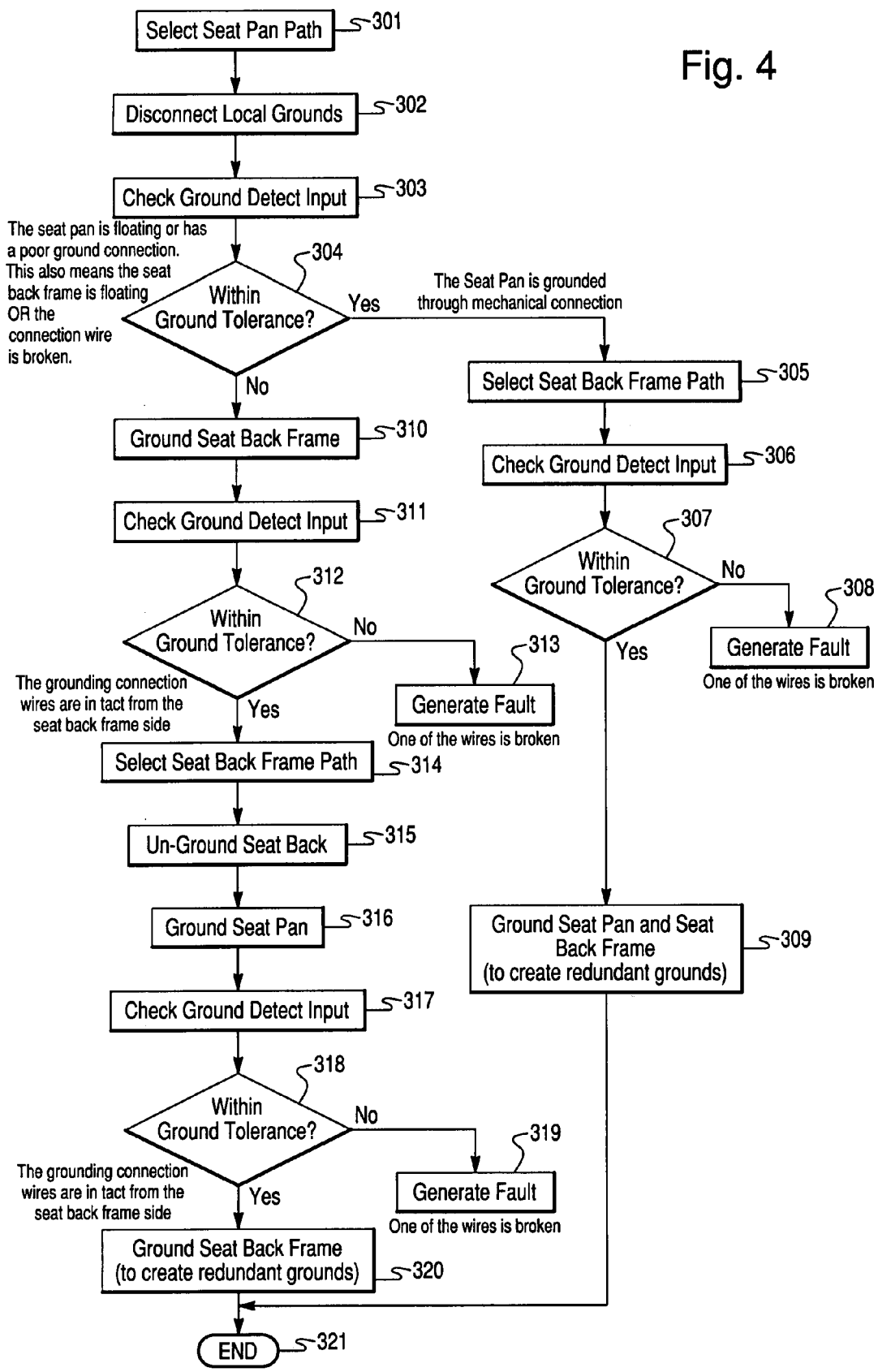
FIG. 4 is a logic flow chart for seat ground detection and verification.

FIG. 4 illustrates the steps in the logic flow path associated with the system shown in FIGS. 2, 3(*a*), 3(*c*). Initially, a seat pan path is selected in step 301. Local grounds are next disconnected in step 302, following this step, ground detection input is checked in step 303.

If the input is within a ground tolerance, as determined in step 304, the seat pan 110 is grounded through mechanical connections and the seat back frame 120 path is then selected in step 305, and ground detection input is checked in step 306. If the input is not within a predetermined ground tolerance as determined in step 307, then an error or fault signal is generated in step 308 to signal that one of the wires 220 is broken. If the input is within the predetermined ground tolerance, then the vehicle seat 100 has a ground seat pan 110 and a ground seat back frame 120, as recognized in step 309, and the logic ends, as shown in step 321.

If, alternatively, the ground detection input is not within the ground tolerance as determined in step 304, then the seat pan 110 is floating or has a poor ground connection. In addition, the seat back frame 120 is floating or the connection wire 220 is broken. Next, the seat back frame 120 is grounded in step 310 and ground detect input is checked in step 311. If the ground detect input is not within the ground tolerance, as determined by step 312, then a fault signal is generated at step 313. In this situation, one of the wires 220 is broken. If the ground detect input is within the ground tolerance, then the seat back frame 120 path is selected in step 314.

The seat back frame 120 is then ungrounded in step 315, and the seat pan is grounded at step 316. In step 317, ground detect input is checked in step 317 and determined if the input is within the ground tolerance in step 318. If the input is not within the tolerance, then a fault is generated to indicate that one of the wires 220 is broken (in step 319). If, however, the input is within the tolerance, then the seat back frame 120 is grounded to create redundant grounds in step 320, and the logic path ends in step 321.

According to another embodiment, there are alternative mechanisms to ground the seat pan 110 and/or seat back frame 120 and still avoid having a system that can undetectably fail because of a single point of failure. For example, multiple grounding wires 220 may be hooked to both the seat pan 110 and seat frame 120, or multiple grounding wires 220 hooked to the seat pan 110 along with multiple wires 225 hooking the seat pan 110 to the seat back frame 120. Alternatively, multiple grounding wires 220 may be hooked to the seat back frame 120 along with multiple wires 225 hooking the seat back frame 120 to the seat pan 110.

In an embodiment, the sensor 270 may be sealed to prevent the sensor 270 from coming into direct contact with wet seat foam of the vehicle seat 100. One exemplary manner of sealing the sensor 270 is to use insulated wire for the sensor 270. The insulation could be PVC, TEFLON® (Polytetrafluoro-ethylene (PTFE) fiber), or any other suitable material. Alternatively, the wire 270 can be sealed at a connection point from the sensor element to the sensor harness by using a dual walled shrink wrap tubing over the entire connection, or by an over-molding over the connection.

Another mechanism for sealing the sensor 270 is to use a conductive layer on a thin carrier substrate (e.g. polyester, KAPTON® (polymide film), or other materials.) The conductor could be screen printed, or adhered in another way to the carrier. Another layer of the carrier can be adhered over the conductor to seal the conductor from water. The connections can be sealed with shrink wrap material or over-molding material.

According to the above embodiments the sensor element 270 can be a separate wire or, according to another embodiment, the sensor 270 may be part of a sensing mat 275, the details of which will be described below.

Figure 5:
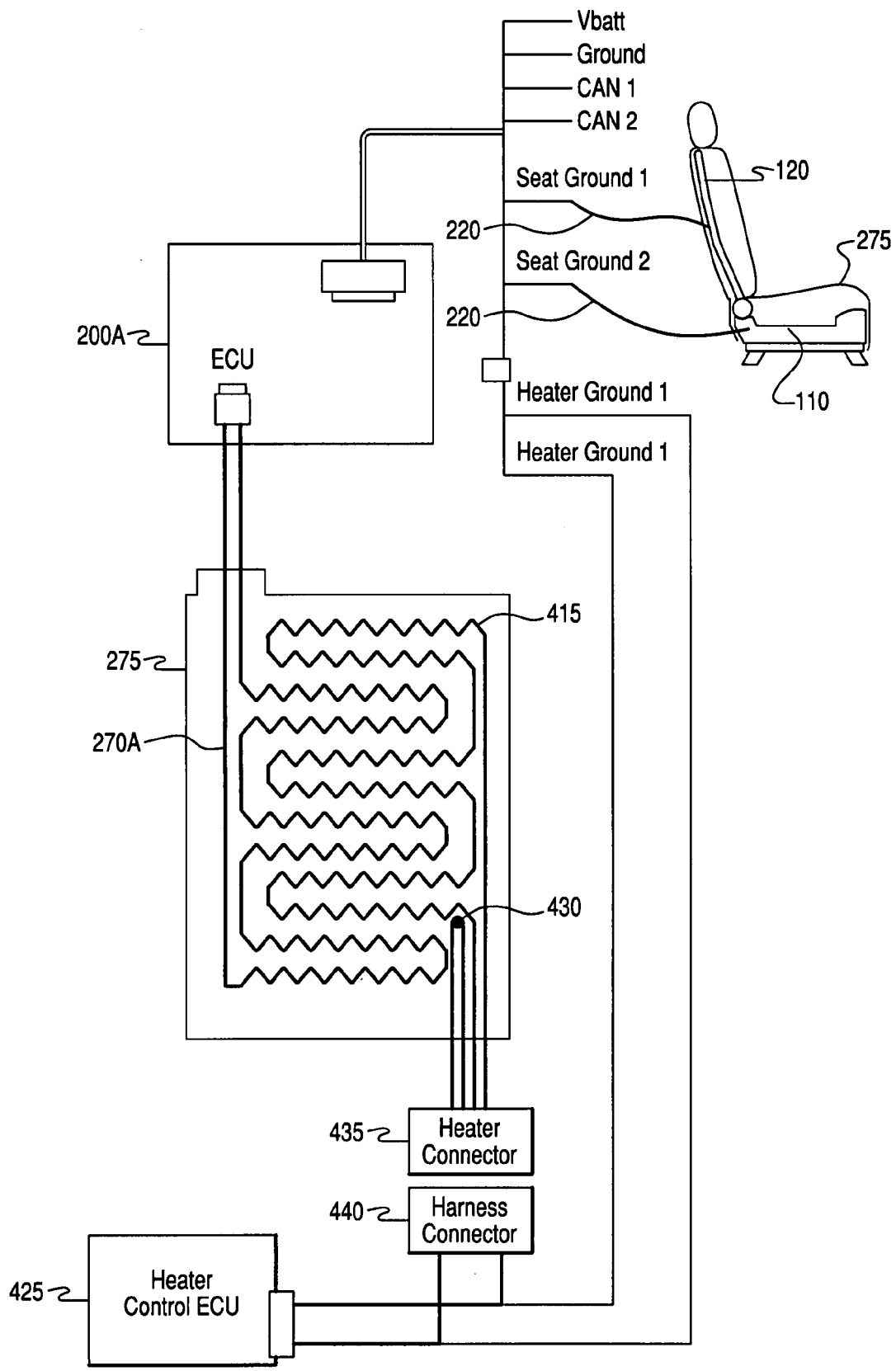
FIG. 5 is a block diagram of an occupant detection system according to one embodiment.

FIG. 5 is a block diagram of an occupant detection system according to one embodiment. As depicted in FIG. 5, the components described below are all mounted in a vehicle seat 100. FIG. 5 shows a sensing mat 275. The sensing mat 275 contains a sensing element 270A and a heating element 415 formed in the sensing mat 275. As shown, the sensing element 270A and heating element 415 do not cross each other. The sensing element 270A and heating element 415 can be made of conventional wire or other conductive materials suitable for vehicle seat applications. The sensing element 270A is configured to obtain capacitive measurements from an occupant sitting in a vehicle seat 100 that are indicative of what type of occupant is in the seat 100 (e.g., a child, infant or adult). The heating element 415 is configured to heat the vehicle seat 100 an thereby providing warmth to an occupant.

According to one embodiment, the sensing element 270A and heating element 415 can be sewn into the sensing mat 275. In addition to the sensing element 270A and heating element 415, a thermistor 30 is mounted on the sensing mat 275 for measuring the temperature of the heating element 415. The sensing element 270A and heating element 415 may be positioned a predetermined distance apart in the sensing mat 275.

Figure 7:
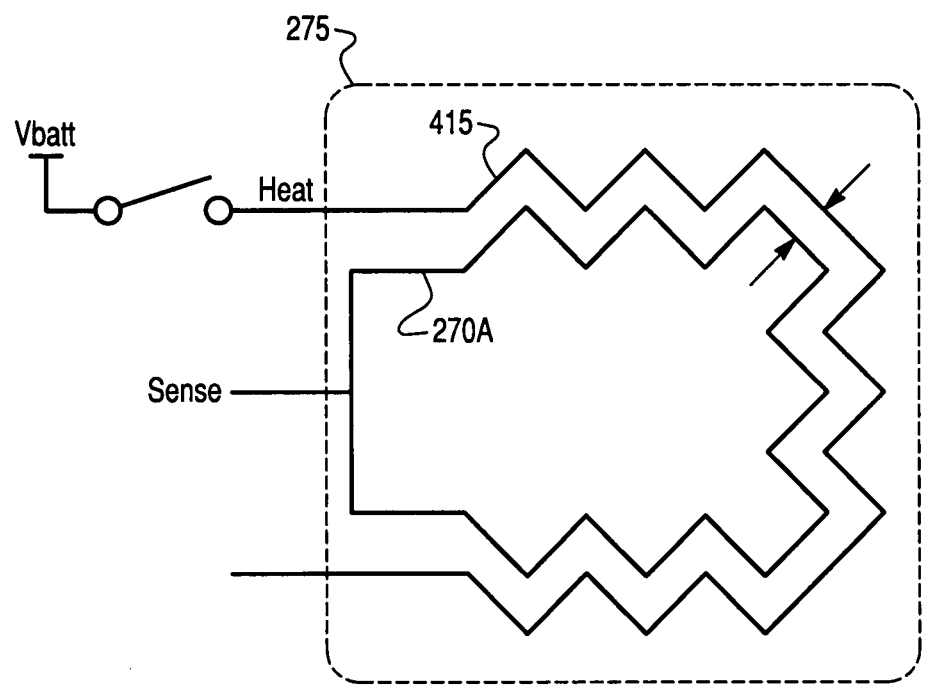
FIG. 7 is shows a sensing mat according to one embodiment.

According to one embodiment, as shown in FIG. 7, the distance between the sensing element 270A and the heating element 415 is sufficient so that the heating signal generated by the heating element 415 has limited impact on the sensing signal generated by the sensing element 270A. However, as the closest conductor to the sensing element 270A, the heating element 415 does influence sensing measurements obtained by the sensing element 270A. For example, the capacitive measurements obtained by the sensing element 270A are larger when the heating element 415 is grounded as opposed to the measurements obtained when the heating element 415 is not grounded. Thus, to make consistent occupant classifications, embodiments will ground the heater element 415 when sensing measurements are taken. The system for grounding the heater element 415 is described in further detail below.

The sensing element 270A on the sensing mat 275 is operably connected to an electronic control unit ECU 200A. According to an embodiment, the sensing element 270A is connected to the ECU 200A via a permanent two-wire connection. The ECU 200A contains control logic for determining the classification of an occupant based on signals received via the sensing elements 10. According to an embodiment, the ECU 200A is a Infant Only Suppression ECU. This type of ECU 200A is designed specifically for infant sensing applications.

Figure 6:
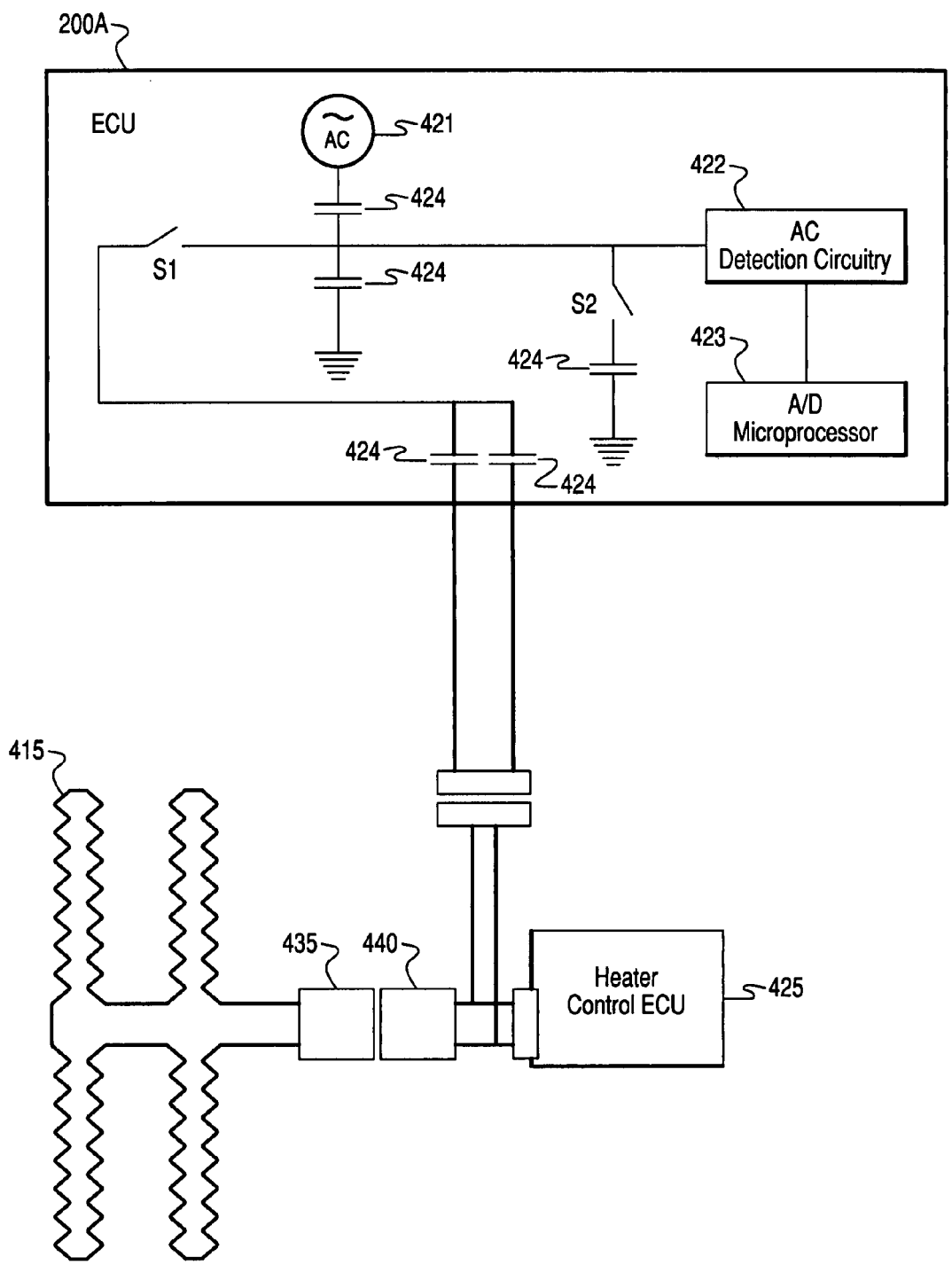
FIG. 6 is a block diagram of a system for monitoring the heating element according to one embodiment.

Similarly, the heating element 415 on the sensing mat 275 is operably connected to a heater controller 425. The heating element 415 can be connected to the heater controller via heater connector 435 and a seat harness connector 440. In addition, the heating element 415 is also connected to the ECU 200A via the seat harness connector 440. As shown in FIG. 6, the ECU 200A contains monitoring circuitry for detecting whether the heating element 415 is grounded.

FIG. 6 is a block diagram of a system for monitoring the heating element 415 according to one exemplary embodiment. It should be understood that the monitoring circuitry can be implemented using numerous circuit designs. The essential function of the monitoring circuitry is to (1) monitor and determine whether the heating element is grounded and (2) if the heating element is not grounded, to ground the heating element (at the sensing frequency) when sensing element 270A is making capacitive measurements.

The monitoring circuitry comprises a signal generator 421, a detection circuit 422, a microprocessor 423 and switches S1 and S2. Various capacitors 424 are arranged throughout the circuit. When S1 is open, the monitoring circuitry can be tested by toggling S2. When S2 is open the detection circuit 422 should receive a strong AC signal. When S2 is closed, the AC signal going to the detection circuit 422 should drop.

When both S1 and S2 are open, the detection circuit 422 should receive a strong AC signal. When S1 is closed, the AC signal received by the detection circuit 422 will drop to about zero if the heating element 415 is grounded. If the heating element 415 is not grounded, the detection circuit 422 will still receive a strong AC signal from the signal generator 421. As stated above, the heating element 415 must be grounded in order for the sensing element 270A to obtain reliable classification signals. Thus, in the event the monitoring circuit determines that the heating element 415 is not grounded, the monitoring circuit grounds the heating element 415 (at the sensing frequency). According to one embodiment, as shown in FIG. 6 this is accomplished by closing switch S2.

Table I below summarizes the functionality of the monitoring circuit depicted in FIG. 6.

TABLE 1

| | | SWITCH S2 | |
|---|---|---|---|
| | | 0 (OPEN) | 1 (CLOSED) |
| SWITCH S1 | 0 | Should sense a strong signal at the detection circuit, otherwise there is a malfunction. | Should sense near-zero at detection circuit, otherwise there is a malfunction. |
| | 1 | ECU should be connected to the heating element. Near-zero signal at the detection circuit means the connection to the heating element is good and the heating element is grounded. Large signal at the detection circuit means the connection to the heating element is broken, or the heating element is not grounded. | The ECU should be connected to the heating element and the heating element should be grounded (at the sensing frequency). If the heating element was grounded when only S1 was closed, then closing S2 redundantly grounds the heating element. If the heating element was not grounded when only s1 was closed, the capacitance measurement should increase when S2 is closed. If this is no the case the there has been a malfunction. |

The above-described apparatus and system can have several advantages. For example, the orientation between the sensing element and heating element is known and fixed. A fixed orientation prevents degradation in performance due to shifts in the orientation of sensing and heating elements observed in conventional systems. Another possible advantage of containing the heating and sensing elements in the same mat is that the heating performance (maximum temperature or time-to-temperature) is not affected by an additional mat above the heater, which is present in most conventional systems. In addition, embodiments can eliminate the possibility of a sensing element being affected by a heating mat being positioned above the sensing element. Further, the need for shielding the sensing element (e.g., with a driven shield) is eliminated because the heating element can be controlled so that it does not significantly affect the capacitive measurements acquired by the sensing element. Finally, the single mat system is easier to install in a vehicle seat than multiple mat systems.

Given the disclosure of the present invention, one versed in the art would appreciate that there may be other embodiments and modifications within the scope and spirit of the invention. Accordingly, all modifications attainable by one versed in the art from the present disclosure within the scope and spirit of the present invention are to be included as further embodiments of the present invention. The scope of the present invention is to be defined as set forth in the following claims.

What is claimed is:

1. An occupant classification system comprising:
a sensing element in a vehicle seat, the sensing element comprises a sensing electrode;
a measurement circuit that is configured to measure a property associated with the sensing electrode;
at least one wire that connects at least one additional conductor to a chassis ground;
a circuit that is configured to determine if the at least one additional conductor is grounded to the chassis ground; and a controller that is configured to classify an occupant by using measurements of the measurement circuit;

wherein the controller includes a mechanism that provides an alternative grounding path to a circuit ground for the at least one additional conductor when circuit determines that the at least one additional conductor is not grounded to the chassis ground.

2. The occupant classification system of claim 1, wherein during a wet seat situation, the controller is configured to separate an adult from a child seat when classifying the occupant.

3. The occupant classification system of claim 2, wherein the sensing electrode is insulated from seat foam and a seat cover of the vehicle seat.

4. The occupant classification system of claim 2, wherein the sensing electrode comprises insulated wire.

5. The occupant classification system of claim 2, wherein the sensing electrode comprises a conductor deposited on a carrier.

6. The occupant classification system of claim 2, wherein the measurement circuit is configured to measure in-phase and quadrature components of the current.

7. The occupant classification system of claim 1, wherein the at least one additional conductor comprises a seat pan and/or seat back frame.

8. The occupant classification system of claim 1, wherein the measurement circuit is configured to measure a current provided to the sensing electrode.

9. The occupant classification system of claim 1, wherein the measurement circuit is configured to perform electric field measurements near the electrode.

10. An occupant classification system for a vehicle seat, comprising:

a conducting sensing electrode;

a controller that is configured to perform electric field measurements near the electrode; and at least one wire to connect the controller to at least one additional conductor wherein the impedance between the additional conductor and a circuit ground influences the electric field measurements, wherein the at least one additional conductor is normally grounded via a normal grounding path that does not include the controller;

wherein the controller includes a mechanism that provides an alternative grounding path via the controller for the at least one additional conductor when the at least one additional conductor is not grounded via the normal grounding path.

11. The occupant classification system of claim 10, wherein the sensing electrode comprises insulated wire.

12. The occupant classification system of claim 10, wherein the sensing electrode comprises a conductor deposited on a carrier.

13. The occupant classification system of claim 10, wherein the sensing electrode is insulated from seat foam and a seat cover of the vehicle seat.

14. The occupant classification system of claim 10, wherein the at least one additional conductor is a heating element.

15. The occupant classification system of claim 10, wherein the at least one additional conductor is a seat pan.

16. The occupant classification system of claim 10, wherein the at least one additional conductor is a seat back frame.

17. The occupant classification system of claim 10, further comprising a sensing mat containing the conducting sensing electrode.

18. An occupant classification system for a vehicle seat, comprising:

a conducting sensing electrode;

a controller configured to measure current sent out to the sensing electrode;

at least one wire to connect the controller to at least one additional conductor wherein the impedance between the additional conductor and a circuit ground influences the measurements of the current to the electrode, wherein the at least one additional conductor is normally grounded via a normal grounding path that does not include the controller;

wherein the controller includes a mechanism that provides an alternative grounding path via the controller for the at least one additional conductor when the at least one additional conductor is not grounded via the normal grounding path.

19. The occupant classification system of claim 18, wherein the at least one additional conductor is a heating element.

20. The occupant classification system of claim 18, wherein the at least one additional conductor is a seat pan.

21. The occupant classification system of claim 18, wherein the at least one additional conductor is a seat back frame.

22. The occupant classification system of claim 18, further comprising a sensing mat containing the conducting sensing electrode.

* * * * *